US010677867B2

(12) United States Patent
Ward et al.

(10) Patent No.: US 10,677,867 B2
(45) Date of Patent: Jun. 9, 2020

(54) MRI-COMPATIBLE 12-LEAD ECG CABLE

(71) Applicant: MiRTLE Medical, LLC, North Andover, MA (US)

(72) Inventors: Jay M. Ward, Stratham, NH (US); Bill Bartula, Merrimac, MA (US); James K. Robertson, Bradford, MA (US); Ronald D. Watkins, Redwood City, CA (US); Ehud J. Schmidt, Newton, MA (US)

(73) Assignee: MIRTLE MEDICAL, LLC, North Andover, MA (US)

( * ) Notice: Subject to any disclaimer, the term of this patent is extended or adjusted under 35 U.S.C. 154(b) by 841 days.

(21) Appl. No.: 15/255,932

(22) Filed: Sep. 2, 2016

(65) Prior Publication Data

US 2017/0067976 A1 Mar. 9, 2017

Related U.S. Application Data

(60) Provisional application No. 62/213,896, filed on Sep. 3, 2015.

(51) Int. Cl.
*A61B 5/04* (2006.01)
*A61B 5/05* (2006.01)
(Continued)

(52) U.S. Cl.
CPC ........ *G01R 33/4808* (2013.01); *A61B 5/0416* (2013.01); *A61B 5/04286* (2013.01);
(Continued)

(58) Field of Classification Search
CPC ........ A61N 1/086; A61N 1/3718; A61N 1/05; A61N 1/08; A61N 1/37; A61N 1/36014;
(Continued)

(56) References Cited

U.S. PATENT DOCUMENTS

| 4,280,507 A | 7/1981 | Rosenberg |
| 6,453,186 B1* | 9/2002 | Lovejoy ............. A61B 5/04085 |
| | | 600/386 |

(Continued)

FOREIGN PATENT DOCUMENTS

| WO | 2007/053507 A1 | 5/2007 |
| WO | WO 2012/145285 A1 | 10/2012 |

(Continued)

OTHER PUBLICATIONS

International Search Report and Written Opinion, Application No. PCT/US2016/150163, dated Mar. 23, 2017.
(Continued)

*Primary Examiner* — Eun Hwa Kim
*Assistant Examiner* — Brian M Antiskay
(74) *Attorney, Agent, or Firm* — Morse, Barnes-Brown & Pendleton, P.C.; Sean D. Detweiler, Esq.

(57) ABSTRACT

An apparatus and method for an electrocardiogram (ECG) cable suitable for use inside a Magnetic Resonance (MR) scanner during a Magnetic Resonance Imaging (MRI) operation. In particular, the present invention relates to a patient safe (MRI-conditional) 12-lead ECG cable capable of use inside an MR scanner during an MRI scan. The ECG cable does not heat up to a degree that would burn a patient undergoing an MRI scan, but also enables the conventional 12-lead ECG electrode placement required for diagnostic monitoring of the patient. Specifically, the ECG cable electrodes can be placed on a patient in the traditional configuration as 12-lead ECG cable designed for use outside of an MR scanner and take diagnostic level readings, during operation of an MR device or system. Additionally, the cable provides a continuous shield which maintains zero emissions while satisfying defibrillation requirements.

17 Claims, 4 Drawing Sheets

(51) Int. Cl.
*G01R 33/48* (2006.01)
*G01R 33/36* (2006.01)
*A61B 5/0416* (2006.01)
*A61B 5/0428* (2006.01)
*A61B 5/055* (2006.01)
*G01R 33/28* (2006.01)

(52) U.S. Cl.
CPC .......... *G01R 33/3685* (2013.01); *A61B 5/055* (2013.01); *A61B 2562/0215* (2017.08); *A61B 2562/0217* (2017.08); *A61B 2562/182* (2013.01); *A61B 2562/222* (2013.01); *G01R 33/288* (2013.01)

(58) Field of Classification Search
CPC .................................................. A61N 1/0476; A61B 5/055; A61B 2090/374; A61B 2018/00839; A61B 2090/3954; A61B 5/04; A61B 2562/227; A61B 5/0006; A61B 5/04012
USPC .......................... 600/372, 382, 384–396, 410
See application file for complete search history.

(56) References Cited

U.S. PATENT DOCUMENTS

| | | | |
|---|---|---|---|
| 7,957,783 | B2* | 6/2011 | Atalar ...................... A61N 1/05 600/374 |
| 2006/0004273 | A1 | 1/2006 | Lobodzinski |
| 2006/0247509 | A1 | 11/2006 | Tuccillo |
| 2010/0217113 | A1 | 8/2010 | Jenkins et al. |
| 2010/0244826 | A1 | 9/2010 | Schmidig |
| 2010/0244977 | A1 | 9/2010 | Feng et al. |
| 2013/0085402 | A1* | 4/2013 | Callahan ............... A61B 5/0402 600/509 |
| 2014/0024909 | A1* | 1/2014 | Vij ........................ A61B 5/055 600/373 |
| 2014/0171783 | A1 | 6/2014 | Schmidt et al. |
| 2014/0303472 | A1 | 10/2014 | Callahan |
| 2014/0309514 | A1 | 10/2014 | Zhou et al. |

FOREIGN PATENT DOCUMENTS

| | | |
|---|---|---|
| WO | WO 2016/122727 A1 | 10/2015 |
| WO | WO 2017/040972 | 3/2017 |

OTHER PUBLICATIONS

International Preliminary Report on Patentability, Application No. PCT/US2016/050163, dated Mar. 15, 2018.

* cited by examiner

MRI-COMPATIBLE 12-LEAD ECG CABLE

CROSS-REFERENCE TO RELATED APPLICATION(S)

This application claims priority to, and the benefit of, U.S. Provisional Application No. 62/213,896, filed Sep. 3, 2015, for all subject matter described therein. The disclosure of said provisional application is hereby incorporated by reference in its entirety.

FIELD OF THE INVENTION

The present invention relates to an electrocardiography cable suitable for use inside a Magnetic Resonance (MR) scanner. In particular, the present invention relates to a Magnetic Resonance Imaging (MRI)-conditional (both MRI-safe and MRI compatible) 12-lead electrocardiography cable capable of use inside an MR scanner during an MRI scan, without reducing the MRI image quality or the MRI interfering with an Electrocardiogram (ECG) signal.

BACKGROUND

Generally, an electrocardiogram (ECG) is used to measure the electrical conduction system of a patient's heart. Primarily ECGs are designed to pick up electrical impulses generated by the polarization and depolarization of cardiac tissues and translate them into a waveform, which is used to measure a rate and regularity of heartbeats. Additionally, ECGs may be used to measure the size and position of the chambers in a patient's heart. Commonly ECGs are used for diagnostic and research purposes.

However, today's ECG technology and devices experience some shortcomings. In particular, current 12-lead ECG recording systems cannot be used in an MRI scanner and cannot produce readable results during an MR imaging session because when the MR scanner is performing a scan, the ECG signal relayed to the ECG recording system by existing ECG cables, is obliterated by electrical signals that are induced from the MR imaging sequence's gradient pulses (typically in the 0-30 KHz frequency band). Additionally, there is risk of the cable and/or the electrode(s) heating from the radio-frequency (RF) waves induced by the RF pulses emanating from the MR scanner. Accordingly, in the construct of the ECG cables, there is a need to utilize only materials that are non-magnetic so that the cable cannot be displaced (pulled, torqued) by the MR scanner's strong static magnetic field. Traditionally, current 12-lead ECGs can be used before and/or after an MRI scan but not during the operation of the MR system.

Alternatively, there are some ECG recording systems capable of operating in and during an MRI scan, but these ECG recording systems are currently restricted in terms of their features and capabilities. In particular, in existing ECG systems that can operate during an MRI scan there are typically only three or four electrodes feeding the ECG recording systems with electrode placements confined to a small area (electrode separation of <10 cm). ECG traces derived from a three or four electrode feed, however, are not of diagnostic grade, meeting specifications which are defined by cardiology or anesthesiology professional societies, and are not as comprehensive as 12-lead ECGs, so they cannot be used to define the location of cardiac events, should they occur in the MRI bore. Instead, three or four lead electrode ECGs are typically limited to detecting the QRS complex and thereby synchronizing the MR imaging to the cardiac cycle. Additionally, three or four lead ECG monitors offer low fidelity signals (a reduced amplitude dynamic range and/or reduced frequency content) that are not suitable for diagnostic-grade applications, such as detecting the onset of acute ischemia. In addition, it is difficult to remove the Magneto-Hydro-dynamic (MHD) voltage from 3-4 lead ECGs. MHD voltage results from the flow of blood inside the MRI's static magnetic field. The MHD voltage peaks during the cardiac cycle's S-wave to T-wave segment ("ST" segment), so it can acutely mask ischemic events, which typically are seen as elevation of the ST segment during this period. MHD voltages are commonly removed using vector-cardiogram (VCG) methods, and the use of 12-lead detection affords improved VCG separation relative to 4-lead systems.

Existing multi-lead electrodes greater than three or four used in generating ECGs cannot be laid out on the chest in the same locations as they are placed outside an MR scanner for patient safety purposes due to radio frequency (RF) energy pickup by the ECG cable's lead wires. In other words, existing lead wires for ECG cables that are capable of being utilized in an MR scanner are too short and they restrict the placement of electrodes to a very tight area to reduce the induced voltages, thereby reducing the energy pickup and thus electrode heating. The short lead wires and tight grouping are necessary for the existing MRI-conditional ECG recording systems to operate safely.

Conventional diagnostic-grade 12-lead ECGs can be used before and/or after MR imaging but not during imaging, which is a substantial shortcoming for many high risk patients (e.g., for patients suffering from Ischemic disease, anesthetized/sedated, or during trauma). Moreover, the American Heart Association (AHA) has defined ECG fidelity criteria that must be present in clinical ECG recording systems. In particular, the criteria defines the maximal allowed noise level in ECG traces (e.g., 50 microvolts), the required frequency spectrum, the minimal level of ST elevation (in mV) that must be seen during acute ischemia, and the maximal level and temporal-frequency of ECG artifacts. As a result of the AHA criteria and the existing MRI-conditional ECG recording system's technological limitations, high risk patients (e.g., patients with ischemic disease, anesthetized/sedated patients, or during trauma) are excluded from MR imaging or from MRI-guided surgery or intervention because they cannot safely monitor the heart during an MRI scan. Accordingly, in view of the above-mentioned limitations, existing ECGs are not sufficient for a cardiologist to accurately assess the physiological state of a patient while they undergo an MR examination.

SUMMARY

There is a need for diagnostic grade high fidelity 12-lead ECGs configured for safe and accurate operation during an MRI scan. The present invention is directed toward solutions to address this need, in addition to having other desirable characteristics. Specifically, the present invention is directed to an ECG cable bundle that protects a patient from being burned while in an MR scanner during imaging while simultaneously providing the traditional 12-lead ECG electrode layout placement required for delivering diagnostic monitoring of the patient. Accordingly, the present invention provides a diagnostic grade 12-lead ECG recording system for use inside an MR scanner during operation, enabling the ability to record high fidelity ECG signals.

In accordance with an embodiment of the present invention, a Electrocardiography (ECG) cable bundle is provided.

The ECG cable bundle includes a plurality of signal leads having proximal ends and distal ends and a plurality of electrodes electrically coupled to the distal ends of the plurality of signal leads, each of the plurality of electrodes being electrically coupled to a different one of each of the plurality of signal leads. The ECG cable bundle also includes a yoke electrically and mechanically coupled to a first end of a cable trunk and a plurality of connectors disposed at the proximal ends of the plurality of signal leads, the plurality of connectors electrically and mechanically coupled to the yoke. The ECG cable bundle further includes a proximal connector electrically and mechanically coupled to a second end of the cable trunk, at least one Radio Frequency (RF) balun interposed on each of the plurality of signal leads between the plurality of electrodes and the yoke, and at least one RF balun interposed on the cable trunk between the yoke and the proximal connector.

In accordance with aspects of the present invention, the at least one RF balun interposed on the cable trunk comprises two or more RF baluns positioned between the first end and the second end of the cable trunk with spacing therebetween. In accordance with aspects of the present invention, the ECG cable bundle is a ten lead cable and the plurality of signal leads each have a predetermined length configuration that structurally enables coexistent placement of one of each of the plurality of signal leads at each of a right arm (RA), a left arm (LA), a left leg (LL), a right leg (RL), a sternal edge right (V1), a sternal edge left (V2), mid-clavicular line left (V4), anterior axillary line (V5), between V2 and V4 (V3), and mid-axillary line left (V6) of a patient.

In accordance with aspects of the present invention, the ECG cable bundle further includes at least one of a plurality of fastening mechanisms attached to each of the distal ends of the plurality of signal leads. In accordance with aspects of the present invention, the plurality of fastening mechanisms are made of carbon fiber. In accordance with aspects of the present invention, the ECG cable bundle reduces interference from an MR scanner during imaging by attenuating radio-frequency energy propagation. In accordance with aspects of the present invention, the plurality of signal leads, the at least one RF balun interposed on each of the plurality of signal leads, the at least one RF balun interposed on the cable trunk, and the cable trunk are made of non-ferrous material.

In accordance with aspects of the present invention, the at least one RF balun can be tuned for a proton Larmor frequency of an MR scanner at a magnetic field of 1.5 T or 3 T MRI using a parallel resonant LCR circuit. In accordance with aspects of the present invention, the plurality of signal leads further comprise resistor pairs, tuned for specific Magnetic Resonance Imaging (MRI) energy. In accordance with aspects of the present invention, the ECG cable bundle operates to transfer ECG signals from a patient during performance of an MRI scan, such that the ECG signals are substantially similar to ECG signals taken outside of an operating MR scanner. In accordance with aspects of the present invention, the ECG cable bundle operates to transfer ECG signals from a patient during performance of an MRI scan without interfering with MR scanner operation.

In accordance with aspects of the present invention, the ECG cable bundle does not interfere with or inhibit performance of an MRI scan on a patient having the ECG cable bundle electrically coupled to the patient and receiving ECG signals from the patient. In accordance with aspects of the present invention, the plurality of electrodes are made of a porous activated carbon with silver-coated films in contact with a silver-chloride gel. In accordance with aspects of the present invention, the at least one of the plurality of connectors and the proximal connector includes a continuous shield to maintain zero emissions.

In accordance with an embodiment of the present invention, a method for performing an electrocardiography (ECG) on a patient during a Magnetic Resonance Imaging (MRI) scan is provided. The method includes placing a plurality of MRI-compatible electrodes on particular locations of the patient, performing the MRI scan of the patient connecting the plurality of MRI-compatible electrodes to an ECG cable bundle, and simultaneous to performing the MRI scan, recording ECG traces.

In accordance with aspects of the present invention, the particular locations include a right arm (RA), a left arm (LA), a left leg (LL), a right leg (RL), a sternal edge right (V1), a sternal edge left (V2), mid-clavicular line left (V4), anterior axillary line (V5), between V2 and V4 (V3), and mid-axillary line left (V6) of the patient. In accordance with aspects of the present invention, the plurality of MRI-compatible electrodes are used for the ECG and do not interfere with the MRI scan. In accordance with aspects of the present invention, the use of the ECG and the plurality of MRI-compatible electrodes do not heat to a temperature that would burn the patient wearing the plurality of MRI-compatible electrodes during the MRI scan. In accordance with aspects of the present invention, the ECG and the plurality of MRI-compatible electrodes do not heat above 1.5 Celsius during a 4 Watt/kg Specific Absorption Rate (SAR) MRI scan.

In accordance with embodiments of the present invention, the present invention can be implemented in any operable combination of claimed features as would be understood by those of skill in the art, such that the present invention is not limited to the specific combinations defined by the claim dependencies as filed.

BRIEF DESCRIPTION OF THE FIGURES

These and other characteristics of the present invention will be more fully understood by reference to the following detailed description in conjunction with the attached drawings, in which.

DETAILED DESCRIPTION

An illustrative embodiment of the present invention relates to an Electrocardiography (ECG) cable suitable for use inside a Magnetic Resonance (MR) scanner for use in Magnetic Resonance Imaging (MRI). In particular, the present invention relates to a 12-lead ECG cable capable of use inside an MR scanner during an MRI sequence while maintaining the safety of the patient from Radio Frequency (RF)-related heating. The 12-lead ECG cable of the present invention includes a plurality of signal leads with copper to carbon fiber splice or connections for attaching a plurality of electrodes. The carbon fiber cable segments, mostly positioned at the distal end of the cable, are utilized to attenuate RF waves at the MRI frequency (typically 61-64 or 123-127 MHz) on the cable, which are induced by the MRI scanner's transmitting body coil. The plurality of signal leads connect to a yoke that is attached to a cable trunk (e.g., a single insulated wire including the plurality of signal leads) that terminates at a proximal connector configured to plug into diagnostic medical devices. The plurality of signal leads and the cable trunk each include one or more Radio Frequency (RF) resonant traps ("baluns") designed to absorb RF energy created during the MRI scan. Additionally, large resistors (e.g., 50 Kilo Ohm) may be placed in the cable leads to further reduce the amplitude of the current flowing through the ECG cables, which can be a potential cause of heating This combination of features enables the ECG cable to provide high fidelity electrical signals from within an MR scanner during an MRI sequence without harming the patient. Additionally, each of the elements of the ECG cable are designed using materials that prevent the generation of heat while inside an MR device, which may otherwise cause harm to a patient, and reduce noise induction into the cables to enable a high fidelity signal to be delivered to the acquisition part ("front-end" or "preamplifier") of the ECG recording system. The combination/configuration of materials in the ECG cable of the present invention forms an ECG system that provides a clean signal outside of an MRI machine as well as while inside and during use of an MR scanner. Note, the terms MRI sequence, MRI operation, MRI scan, and variations thereof, are utilized interchangeably herein to indicate the process of the MR scanner, device, or system, in operation.

Prior to the present invention, conventional ECG cables were not designed to provide a readable ECG signal from within an MR device and/or during an MRI scan. In particular, when the MR scanner is performing a scan, the ECG signal, provided by conventional ECG cables, is overlaid with additional induced signals from the MR imaging sequence, and thus does not provide a readable signal. Additionally, these conventional ECG cables can heat up during MRI scans, sometimes to the extent where they can create skin burns on the patient at the location of the ECG electrodes, because the ECG lead wires receive induced RF energy. Furthermore, the use of traditional ECG cables during an MRI can be harmful to a patient and does not provide a readable high fidelity signal that is useful for diagnostic purposes, as discussed herein.

In accordance with an example embodiment of the present invention, the shortcomings of conventional ECG cables are solved by implementing hardware (e.g., filters and switches and adding resistors to both signal and shield conductors) in accordance with the present invention to reduce interference (e.g., created by the MR scanner). For example, the shortcomings of conventional ECG cables are overcome by creating an ECG cable bundle from a non-ferrous RF balun tuned to the MR scanner's field strength. This combination of hardware and materials results in an ECG cable bundle that is safe for use within an MR scanner and provides a high fidelity ECG signal suitable for diagnostic purposes during MR imaging. Enabling the use of a high fidelity ECG recording system during an MRI scan can provide benefits for patients suffering from a variety of conditions. As would be appreciated by one skilled in the art, these patients can include high risk patients with conditions related to ischemic disease, anesthetized/sedated (pediatric, stroke), during trauma, or atrial or ventricular arrhythmia patients, since unsteady rhythm leads to blurred cardiac MR images, since these must be properly synchronized to the cardiac cycle.

Additionally, the use of an ECG recording system during an MRI scan also enables a number of procedures previously unavailable to practitioners. For example, procedures such as MRI-guided intervention (surgery) on the heart, brain, and abdomen can be performed in accordance with the present invention. Accordingly, the device of the present invention provides a vast improvement to medical diagnostic testing and to medical therapy, in particular to the use of ECG and MRI tests and related procedures.

FIGS. 1 through 4, wherein like parts are designated by like reference numerals throughout, illustrate an example embodiment or embodiments of a 12-lead ECG cable capable of use inside an MR scanner during an MRI sequence without harming the patient, according to the present invention. Although the present invention will be described with reference to the example embodiment or embodiments illustrated in the figures, it should be understood that many alternative forms can embody the present invention. One of skill in the art will additionally appreciate different ways to alter the parameters of the embodiment(s) disclosed, such as the size, shape, or type of elements or materials, in a manner still in keeping with the spirit and scope of the present invention.

Figure 1:
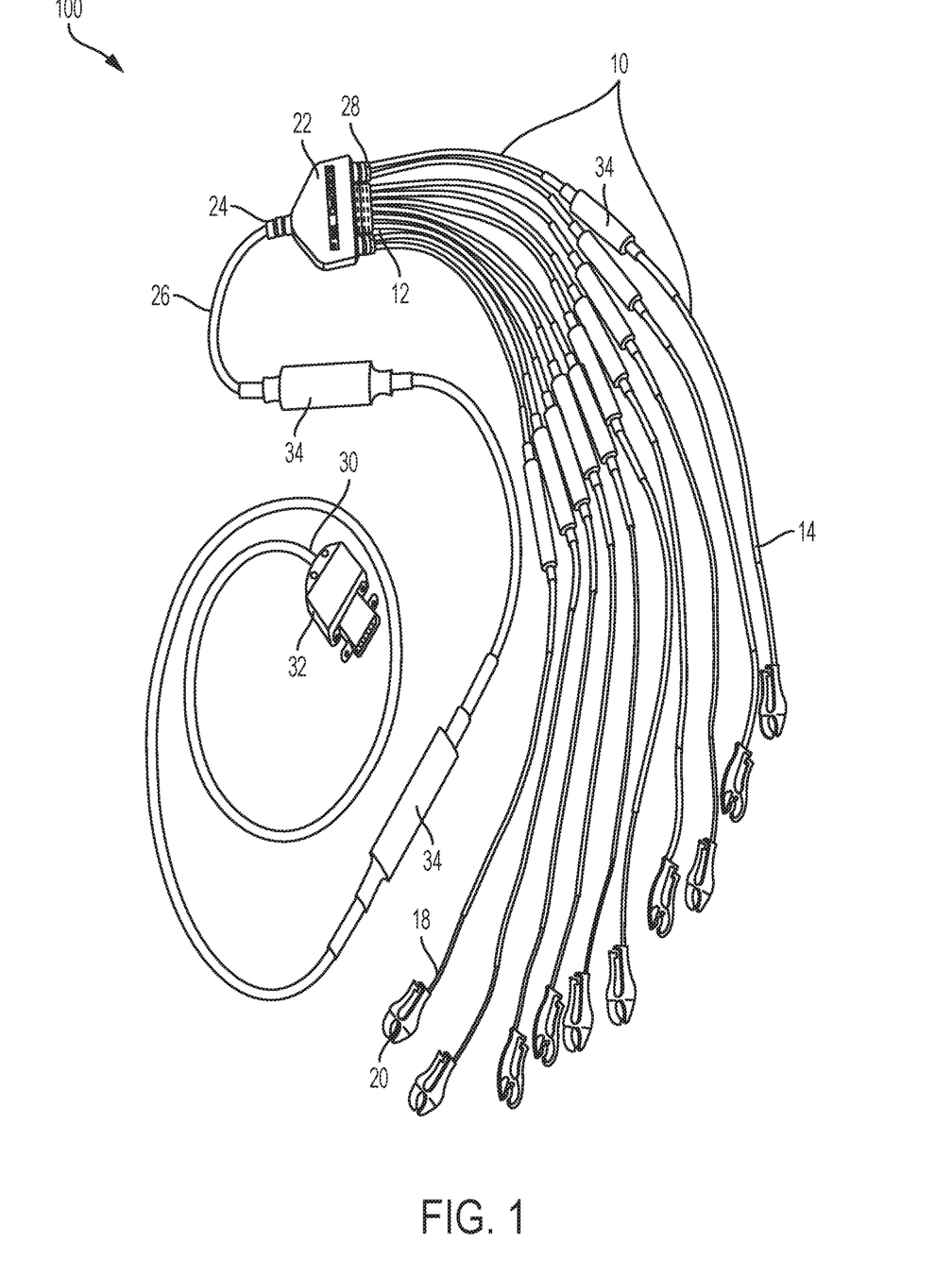
FIG. 1 is an illustration of the 12-lead ECG cable, in accordance with the present invention.
Figure 2:
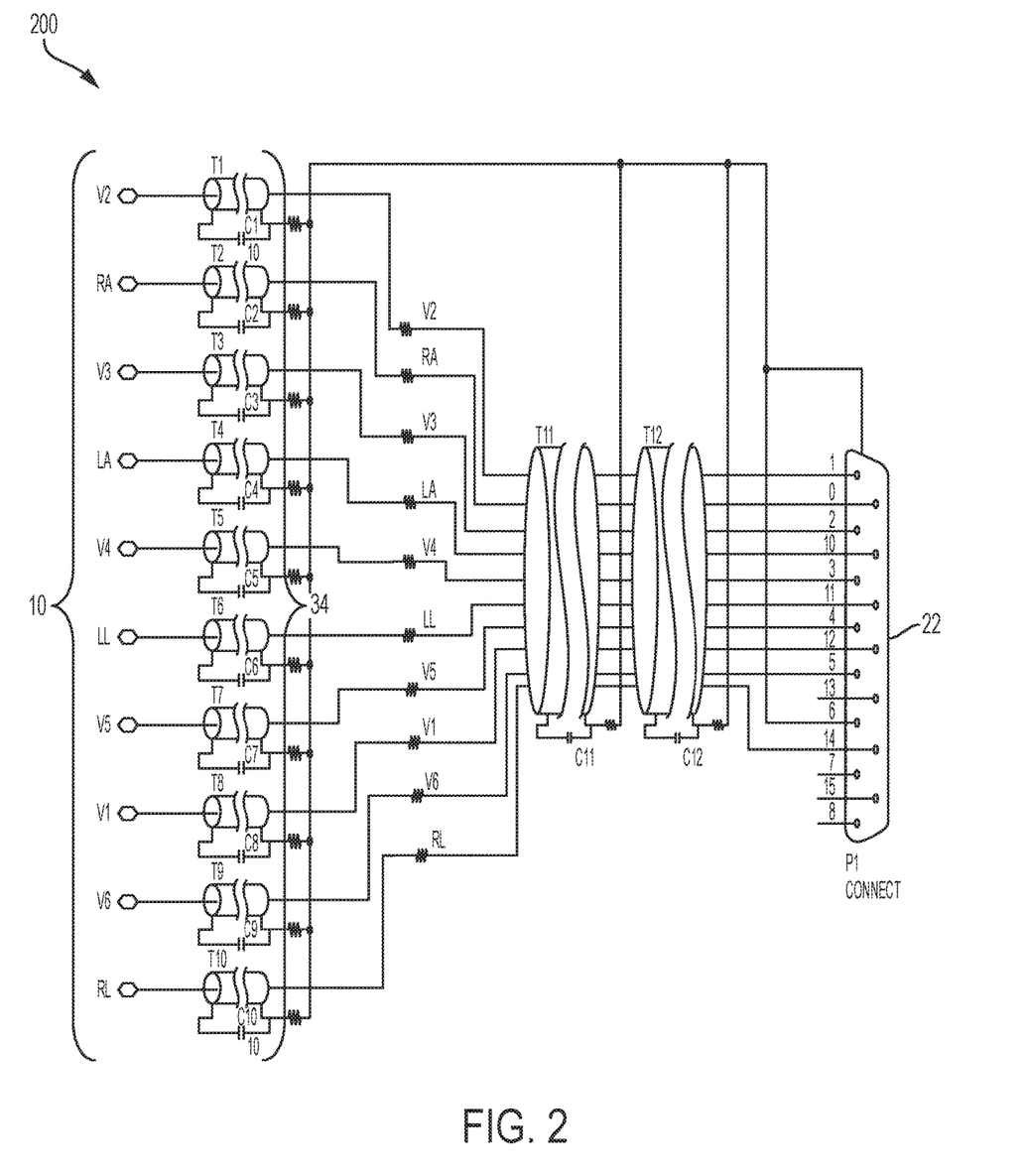
FIG. 2 is an electrical schematic of the 12-lead ECG cable, in accordance with the present invention.
Figure 3:
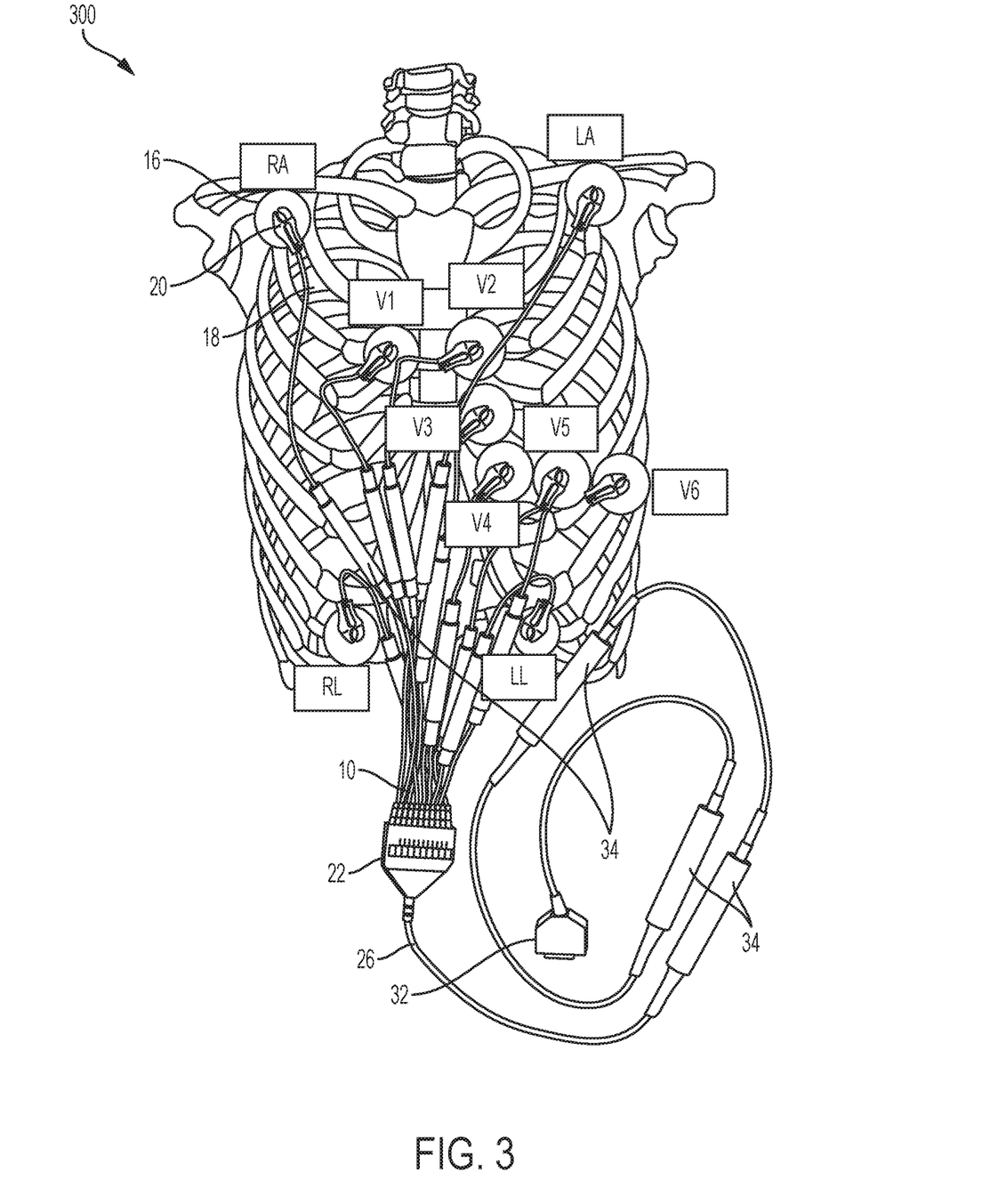
FIG. 3 is an illustration of the varying lengths of the leads for the 12-lead ECG cable and the specific placement of those leads on a patient, in accordance with the present invention.

Referring now to FIGS. 1-3, a 12-lead Electrocardiography (ECG) cable bundle 100 suitable for use on a patient during operation of an MRI device or system is depicted in accordance with an example embodiment of the present invention. In particular, FIG. 1 depicts the ECG cable bundle 100 and the elements that create the ECG cable bundle 100. FIG. 2 depicts an electrical diagram of aspects of the ECG cable bundle 100 and FIG. 3 depicts the ECG cable bundle 100 as it would be positioned on a patient during use. As would be appreciated by one skilled in the art, although the present invention is described herein for safe use in an MR scanner and during an MRI scan, the invention is not intended to be limited only to use in a MR scanner or during an MRI scan. For example, the ECG cable bundle 100 of the present invention can be used effectively outside of an MR scanner and can be used to perform ECG recording as would be performed with a traditional ECG cable bundle, separate from operation in an MRI device or system. The description of the ECG cable bundle is discussed with respect to FIGS. 1-3.

In accordance with an example embodiment of the present invention, the ECG cable bundle 100 includes a plurality of signal leads 10 having proximal ends 12 and distal ends 14. The plurality of signal leads 10 are made of a low impedance material. For example, the plurality of signal leads 10 can be made of 50 ohm (specific impedance) coaxial cables. In accordance with an example embodiment of the present invention, a plurality of electrodes 16 are electrically coupled to the distal ends 14 of the plurality of signal leads 10, as shown in FIG. 3. As would be appreciated by one skilled in the art, each of the plurality of electrodes 16 can be electrically coupled to a different one of each of the plurality of signal leads 10. For example, the plurality of electrodes 16 can be coupled to the plurality of signal leads 10 through copper to carbon fiber splice or connections 18. The copper or carbon fiber splice connections facilitate prevention of heat generation, which prevents burning of a patient's skin during an MR imaging sequence. In particular, the carbon fiber cable segments are utilized to attenuate RF waves at the MRI frequency (typically 61-64 or 123-127 MHz) on the cable, which are induced by the MRI scanner's transmitting body coil. Similarly, the plurality of electrodes 16 can be made with materials with heat generation preventative properties. Specifically, the electrodes 16 are made of porous non-ferrous materials, such as porous activated carbon, and utilize silver-coated films in contact with a silver-chloride gel to perform efficient ionic-electronic energy conversion.

In accordance with an example embodiment of the present invention, the ECG cable bundle 100 also includes at least one of a plurality of fastening mechanisms 20 attached to each of the distal ends 14 of the plurality of signal leads 10. The fastening mechanisms 20 are configured to attach the plurality of electrodes 16 to the distal ends 14 of the plurality of signal leads 10. As would be appreciated by one skilled in the art, the plurality of electrodes 16 are attached to the plurality of signal leads 10 using a variety of different types of fastening mechanisms 20. For example, the fastening mechanisms 20 can include clips, snaps, hook and loop fasteners, etc. In accordance with an example embodiment of the present invention, the plurality of fastening mechanisms 20 are made of carbon fiber. The use of carbon fiber assists in the reduction of interference from an MR scanner during imaging relative to conventional ECG wire bundles since it attenuates radio-frequency (typically 61-64 or 123-127 MHz) energy propagation. As would be appreciated by one skilled in the art, the fastening mechanisms 20 can be made of any material known in the art that reduces interference and heat during operation of an MR scanner. For example, the fastening mechanisms 20 can be constructed of any material that is known in the art to have radio transparent qualities and also be capable of performing the necessary operations of ECG leads or wire bundles, as would be appreciated by those of skill in the art.

In accordance with an example embodiment of the present invention, the ECG cable bundle 100 further includes a yoke adapter 22, which is electrically and mechanically coupled to a first end 24 of a cable trunk 26. The cable trunk 26 can include the plurality of signal leads 10 in a single insulated wire. As would be appreciated by one skilled in the art, the plurality of signal leads 10 can be included in the cable trunk 26 until they branch off into separate leads from the yoke adapter 22. Accordingly, the yoke adapter 22 can include inputs for a plurality of connectors 28 disposed at the proximal ends 12 of the plurality of signal leads 10, such that the plurality of connectors 28 electrically and mechanically couple the plurality of signal leads 10 to the yoke adapter 22. For example, the yoke adapter 22 can include standardized female inputs with a specific configuration as used in the industry and known by those of skill in the art. As would be appreciated by one skilled in the art, the yoke adaptor 22 splits the electrical connections for each respective signal lead 10, included within the cable trunk 26, to the separate signal leads 10 at the plurality of connectors 28.

In accordance with an example embodiment of the present invention, a second end 30 of the cable trunk 26 can be electrically and mechanically coupled to a proximal connector 32 (e.g., an ECG adaptor). As would be appreciated by one skilled in the art, the proximal connector 32 can be configured to plug into various types of monitoring equipment for receiving, recording, analyzing, and/or displaying signals received from the ECG cable bundle 100. For example, the proximal connector 32 can be configured to be plugged into an amplifier and/or a conventional ECG monitor designed to receive, process, and display signals from the plurality of electrodes 16. In accordance with an example embodiment of the present invention, the proximal connector 32 and/or the plurality of connectors 28 include a continuous shield from their respective housings to the cable shielding (e.g., around the cable trunk 26 and signal leads 10). The continuous shield maintains "zero" emissions, which as utilized herein is defined as less than −120 decibel amplitude RF signal at the MRI's Larmor frequency, so that there is no noticeable reduction in an MRI image's signal to noise ratio (relative to a situation where the ECG system is absent), from the ECG cable bundle 100 while satisfying defibrillation requirements. The continuous shield wraps on the outside of the proximal connector 32 and/or the plurality of connectors 28 utilizing an Electromagnetic Interference (EMI) gasket on the ECG cable bundle's 100 socket (e.g., plug of the proximal connector 32).

In accordance with an example embodiment of the present invention, the ECG cable bundle 100 can include at least one RF balun 34 (e.g., Resonant RF cable traps or radio frequency tuned baluns) interposed on/within each of the plurality of signal leads 10 between the plurality of electrodes 16 and the yoke adapter 22. Additionally, the ECG cable bundle 100 can also include at least one RF balun 34 interposed on the cable trunk 26 between the yoke adapter 22 and the proximal connector 32. As would be appreciated by one skilled in the art, the at least one RF balun 34 can include any combination of number of RF baluns and can be placed at different locations between the proximal connector 32 and the plurality of electrodes 16. For example, the at least one RF balun 34 interposed on the cable trunk 26 of the ECG cable bundle 100 can include two or more RF baluns positioned between the first end 24 and the second end 30 of the cable trunk 26 with spacing there between, as depicted in FIG. 1.

In accordance with an example embodiment of the present invention, the at least one RF balun 34 can be specifically tuned to provide a reduction in RF propagation on the cables, and thus reduce heat resulting in improved signal quality for the ECG cable bundle 100 while it is located inside an MR scanner during imaging. For example, the at least one RF balun 34 can be tuned for the proton Larmor frequency of the MRI at a magnetic field of 1.5 T or 3 T MRI (e.g. 64 or 137 MHz) using a parallel resonant Inductor, Capacitor, Resister (LCR) circuit. Accordingly, the at least one RF balun 34 in combination with the other elements of the ECG cable bundle 100 enables the ECG cable bundle 100 to be safely used in an MR scanner during operation without causing harm to a patient, and while providing high fidelity readable signals for diagnostics (e.g., via an ECG recording systems). In accordance with an example embodiment of the present invention, the plurality of signal leads 10, the at least one RF balun 34 interposed on each of the plurality of signal leads 10, the at least one RF balun 34 interposed on the cable trunk 26, and the cable trunk 26 are made of non-ferrous material. As would be appreciated by one skilled in the art, the purpose of the at least one RF balun 34 is to prevent (radio frequency) RF energy from propagating on the cable (e.g. by attenuating it) thereby causing burning to the patient during an MRI scan.

In accordance with an example embodiment of the present invention, the plurality of signal leads 10 in the ECG cable bundle 100 includes ten lead cables and each signal lead 10 cable has a predetermined length configuration that structurally enables coexistent placement of one of each of the electrodes 16 of the plurality of signal leads 10 particular locations on a patient. FIG. 3 depicts ideal placement locations of a right arm (RA), a left arm (LA), a left leg (LL), a right leg (RL), a sternal edge right (V1), a sternal edge left (V2), mid-clavicular line left (V4), anterior axillary line (V5), between V2 and V4 (V3), and mid-axillary line left (V6) of a patient in accordance with conventional 12-lead ECG cable placement. In accordance with an example embodiment of the present invention, the ECG cable bundle 100 includes resistor pairs, tuned for specific Magnetic Resonance Imaging (MRI) energy. The resistor pairs can be disposed at different locations within the ECG cable bundle 100. For example, a first resistor can be included in the yoke adaptor 22 and a second resistor can be included in the proximal connector 32. As would be appreciated by one skilled in the art, the resistor pairs can be tuned for the receiving frequency of the MRI, and can differ based on MRI strength. For example, the tuning for 3 T MRIs is 123-127 MHz & for 1.5 T 61-64 MHz.

In operation, the present invention relates to a patient safe (MRI conditional) 12-lead ECG cable bundle 100 capable of being used inside an MR device or system during an MRI scan. The ECG cable bundle 100 does not interfere with or inhibit performance of an MRI scan on a patient. In particular, the ECG cable bundle 100 can safely be electrically coupled to the patient and transmit ECG signals from the patient to an ECG device. The ECG cable bundle 100 is configured to transfer ECG signals from the electrodes 16 placed on the patient during performance of an MRI scan, such that the ECG signals are substantially similar to ECG signals taken outside of the MRI scan. In the context utilized here, "substantially" means that diagnostic level readings can be obtained using the ECG cable bundle 100 of the present invention during MRI scan. Accordingly, the ECG cable bundle 100 can be used to monitor and provide clear signals for at risk heart conditions or particular states of the heart during an MRI scan. As would be appreciated by one skilled in the art, the ECG cable bundle 100 can be used for normal heart monitoring either inside or outside of an MR scanner.

The combination of elements that make up the cable bundle 100, as depicted in FIGS. 1-3 provide a variety of advantages and improvements over existing ECG cables. The cables reduce the propagation of radio-frequency waves at the MRI's operating frequency (e.g. Larmor frequency, typically 63 or 124 MHz). This enables a digital ECG recording system to meet the IEC/NEMA limits for MRI-related heating, which are <1.5 degree Celsius temperature increase during a 4.0 Watt/kg MRI pulse sequence, with the cable bundle 100 signal leads 10 spread out over a patient's anterior chest in the classical 12-lead configuration (as depicted in FIG. 2), which typically covers a 40 cm Superior-Inferior, and a 40 cm Left-Right distance.

Additionally, the cable bundle 100 enables an MRI-compatible digital ECG system to meet AHA ECG fidelity specifications, as outlined in AHA documents. The specifications include standards for the minimal resolved ECG signal above a noise level, standards for a minimal observed size of ST elevation during acute ischemia, as well as standards on an amplitude and frequency content of an ECG signal. Satisfaction of these standards by the cable bundle 100 of the present invention can be confirmed when the cable bundle 100 is used to acquire ECG data without an MRI scanner pulsing (acquiring data), or when the cable bundle 100 is used outside an MRI bore. The cable bundle 100 also enables an MRI-compatible digital ECG system to meet the requirements for surface ECG measurements performed during cardiac electrophysiological interventional procedures for treatment of arrhythmia which are both performed inside an MRI scanner. (The surface ECGs are then combined with measurement of intra-cardiac ECG signals for purposes of synchronization, and understanding of the patient's clinical state during the procedure).

When used in combination with an MRI scanner, the cable bundle 100 permits an MRI-compatible digital ECG system to capture the full frequency (from DC up to 50 KHz) and amplitude (from 50 microvolts up to 20 Volts Peak-to-Peak) spectrum of the gradient induced voltages (GIVs) generated during the execution of MRI pulse sequences. As would be appreciated by one skilled in the art, the GIVs appear as overlays on ECG traces acquired inside the MRI scanner. The overlays provided by utilization of the cable bundle 100 during an MRI are far larger than ECG traces acquired in the absence of the MRI pulsing, so that acquiring their full spectrum allows for utilization of several methods for their subsequent removal, resulting in the recording and display of clean ECG traces inside the MRI bore. Accordingly, the cable bundle 100 enable an MRI-compatible digital ECG system to capture the full amplitude of the Magneto-hydrodynamic (MHD) signal generated whenever ECG traces are acquired inside the MRI bore (even without the MRI pulsing). As an example, the MHD voltages appear as overlays on ECG traces acquired inside the MRI scanner, and since they occur during the ECG's S-wave to T-wave interval ("ST segment"), the traces can mask ischemic events, which are mainly seen in ECG traces during this period in the cardiac cycles. These MHD overlays may be larger than the amplitude of the QRS complex in ECG traces acquired outside the MRI scanner, especially at higher MRI fields, so that they also prevent synchronization of the MRI scanner to the cardiac cycle, which is frequently performed by detecting the QRS wave. As a result, acquiring the full amplitude of the MHD allows for utilization of several methods for the subsequent MHD removal, such as performed by using Vector ECG methods ("VCG" methods), resulting in the recording and display of clean ECG traces inside the MRI bore, which properly visualize the ST segment of the cardiac cycle, as well as allowing for cardiac synchronization of the MRI scanner from the 12-lead ECG.

Overall, the cable bundle 100 enables an ECG system to be used during MRI imaging, without noticeably reducing the imaging signal-to-noise ratio (SNR). This functionality is accomplished by adding specific devices that prevent RF interference (RFI) from exiting the ECG system's electronics and propagating on the ECG cable, and thereby into the MRI scanner's bore. This "zero emission" property of the cable bundle 100 is readily observed when comparing the SNR quality of MRI images acquired with the 12-lead MRI-compatible ECG system shut to those acquired with the 12-lead ECG system working.

Figure 4:
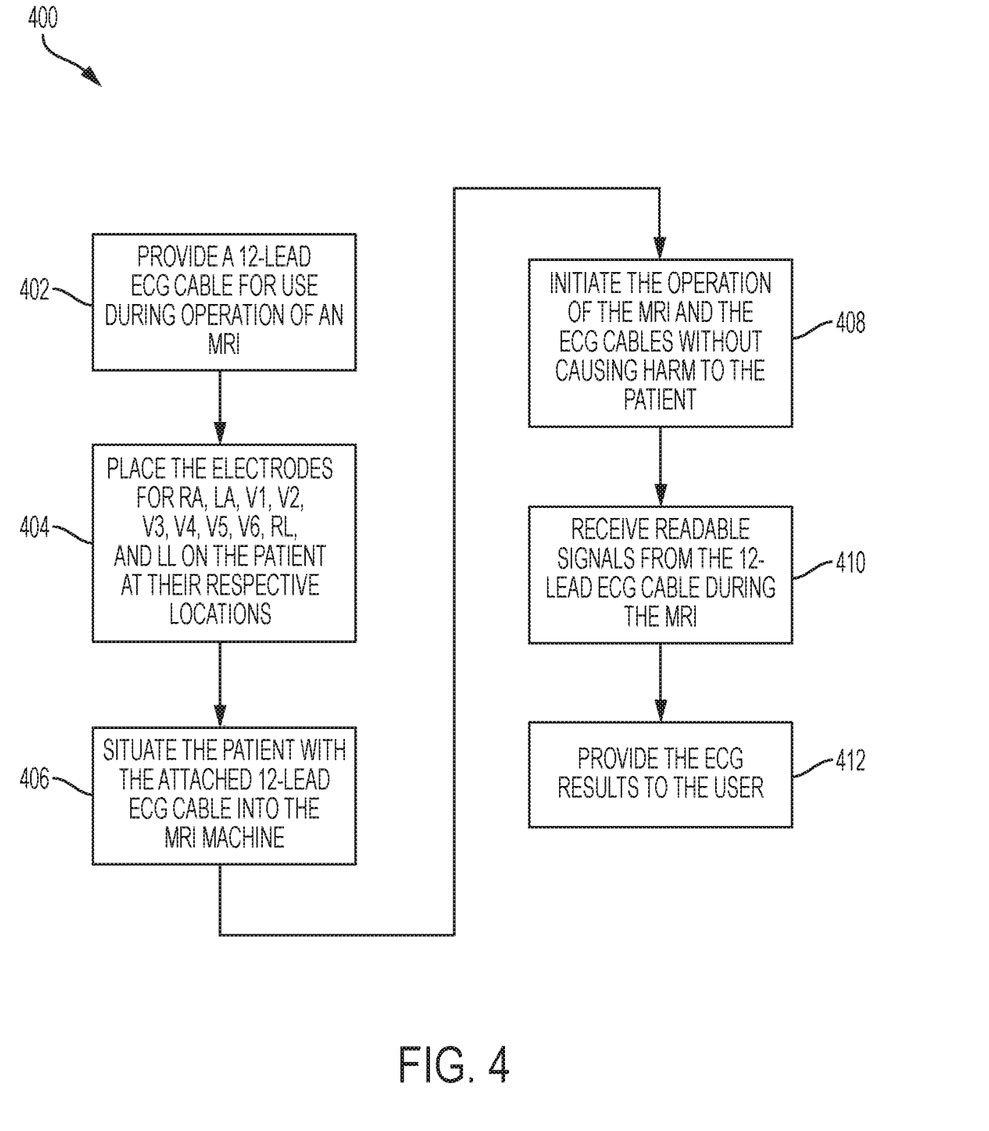
FIG. 4 is a method for implementing the 12-lead ECG for use during an MRI scan, in accordance with the present invention.

FIG. 4 depicts a method for using the ECG cable bundle 100 during the operation of an MR scanner, in accordance with the present invention. In particular, process 400 depicts a method for performing an electrocardiography on a patient during a MRI scan. At step 402, a 12-lead ECG cable bundle (e.g., the ECG cable bundle 100) is provided for use during an MRI scan. At step 404, a user (e.g., a physician or clinical worker) can place a plurality of electrodes (e.g., electrodes 16) on particular locations on a patient's chest, as depicted in FIG. 3. As would be appreciated by one skilled in the art, the placement of the electrodes 16 on the patient can include the traditional placements of the electrodes 16 for an ECG on a patient outside of an MRI scan. For example, the particular placement locations can include a right arm (RA), a left arm (LA), a left leg (LL), a right leg (RL), a sternal edge right (V1), a sternal edge left (V2), mid-clavicular line left (V4), anterior axillary line (V5), between V2 and V4 (V3), and mid-axillary line left (V6) of the patient.

Continuing with FIG. 4, and in accordance with an example embodiment of the present invention, at step 406, the user can initiate and perform the MRI scan of the patient. For example, the user can place the patient in the MR scanner and initiate the MRI scan as it is performed traditionally. The construction and combination of materials of the ECG cable bundle 100 enables ECG monitoring during an MRI scan without the MR scanner harming ECG trace quality or vice versa. At step 408, simultaneous to performing the MRI scan, the user can also initiate operations of ECG recording systems. The ECG can operate during the MRI scan without the 12-lead ECG cable bundle 100 causing harm to the patient or interfering with the MR scanner operation. For example, the structure of the ECG cable bundle 100, as described with respect to FIGS. 1-3, prevents the 12-lead ECG cable bundle 100 from overheating (e.g., due to radio frequency energy) and burning the patient. The series of RF tuned balun(s) (e.g., at least one RF balun 34) eliminate RF energy, which is coupled into the cable, and thus eliminate burning the patient. Accordingly, the ECG cable bundle 100 meets the Food and Drug Administration's (FDA) limit of <1.5 Celsius temperature increase during a 4 Watt/kg Specific Absorption Rate (SAR) MRI scan.

At step 410, an ECG monitoring device connected to the 12-lead ECG cable (e.g., through proximal connector 32) can receive high fidelity readable signals during the MRI scan without interfering with the operation of the MR scanner or the results of the MRI scan. For example, an ECG recording system can receive high fidelity readable signals in accordance with the AHA defined ECG fidelity criteria. Additionally, the 12-lead ECG cable attached to the patient used does not interfere with the MRI scan or the results of the MRI scan. As step 412, the results of the MRI scan and ECG can be provided to the user. For example, the results can be displayed in a traditional format as would have been displayed if the tests were performed separately (e.g., the ECG results would be displayed on an Electrocardiograph monitor). As would be appreciated by one skilled in the art, the test results could be displayed simultaneously on a single display device. In accordance with an example embodiment of the present invention, the process 400 of FIG. 4 can be adapted for use as a traditional ECG cable. In particular, the steps related to the MR scanner and MRI operation can be omitted for monitoring patients not inside an MR scanner.

As utilized herein, the terms "comprises" and "comprising" are intended to be construed as being inclusive, not exclusive. As utilized herein, the terms "exemplary", "example", and "illustrative", are intended to mean "serving as an example, instance, or illustration" and should not be construed as indicating, or not indicating, a preferred or advantageous configuration relative to other configurations. As utilized herein, the terms "about" and "approximately" are intended to cover variations that may existing in the upper and lower limits of the ranges of subjective or objective values, such as variations in properties, parameters, sizes, and dimensions. In one non-limiting example, the terms "about" and "approximately" mean at, or plus 10 percent or less, or minus 10 percent or less. In one non-limiting example, the terms "about" and "approximately" mean sufficiently close to be deemed by one of skill in the art in the relevant field to be included. As utilized herein, the term "substantially" refers to the complete or nearly complete extend or degree of an action, characteristic, property, state, structure, item, or result, as would be appreciated by one of skill in the art. For example, an object that is "substantially" circular would mean that the object is either completely a circle to mathematically determinable limits, or nearly a circle as would be recognized or understood by one of skill in the art. The exact allowable degree of deviation from absolute completeness may in some instances depend on the specific context. However, in general, the nearness of completion will be so as to have the same overall result as if absolute and total completion were achieved or obtained. The use of "substantially" is equally applicable when utilized in a negative connotation to refer to the complete or near complete lack of an action, characteristic, property, state, structure, item, or result, as would be appreciated by one of skill in the art.

Numerous modifications and alternative embodiments of the present invention will be apparent to those skilled in the art in view of the foregoing description. Accordingly, this description is to be construed as illustrative only and is for the purpose of teaching those skilled in the art the best mode for carrying out the present invention. Details of the structure may vary substantially without departing from the spirit of the present invention, and exclusive use of all modifications that come within the scope of the appended claims is reserved. Within this specification embodiments have been described in a way that enables a clear and concise specification to be written, but it is intended and will be appreciated that embodiments may be variously combined or separated without parting from the invention. It is intended that the present invention be limited only to the extent required by the appended claims and the applicable rules of law.

It is also to be understood that the following claims are to cover all generic and specific features of the invention described herein, and all statements of the scope of the invention which, as a matter of language, might be said to fall therebetween.

What is claimed is:

1. An electrocardiography (ECG) cable bundle, comprising:
   a plurality of signal leads, each of the plurality of signal leads having a proximal end and a distal end, wherein the plurality of signal leads further comprise resistor pairs disposed at different locations, tuned for specific magnetic resonance imaging (MRI) energy;
   a plurality of electrodes electrically coupled to the distal ends of the plurality of signal leads, each of the plurality of electrodes being electrically coupled to a different one of each of the plurality of signal leads;
   at least one of a plurality of fastening mechanisms attached to each of the distal ends of the plurality of signal leads;
   a yoke electrically and mechanically coupled to a first end of a cable trunk;
   a plurality of connectors disposed at the proximal ends of the plurality of signal leads, the plurality of connectors electrically and mechanically coupled to the yoke;
   a proximal connector electrically and mechanically coupled to a second end of the cable trunk;
   at least one radio frequency (RF) balun interposed on each of the plurality of signal leads between the plurality of electrodes and the yoke; and
   at least one RF balun interposed on the cable trunk between the yoke and the proximal connector creating a series of RF baluns.

2. The ECG cable bundle of claim 1, wherein the at least one RF balun interposed on the cable trunk comprises two or more RF baluns positioned between the first end and the second end of the cable trunk with spacing therebetween.

3. The ECG cable bundle of claim 1, wherein the ECG cable bundle is a ten lead cable and the plurality of signal leads each have a predetermined length configuration that structurally enables coexistent placement of one of each of the plurality of signal leads at each of a right arm (RA), a left arm (LA), a left leg (LL), a right leg (RL), a sternal edge right (V1), a sternal edge left (V2), mid-clavicular line left (V4), anterior axillary line (V5), between V2 and V4 (V3), and mid-axillary line left (V6) of a patient.

4. The ECG cable bundle of claim 1, wherein the plurality of fastening mechanisms are made of carbon fiber.

5. The ECG cable bundle of claim 1, wherein the ECG cable bundle reduces interference from a magnetic resonance (MR) scanner during imaging by attenuating radio-frequency energy propagation.

6. The ECG cable bundle of claim 1, wherein the plurality of signal leads, the at least one RF balun interposed on each of the plurality of signal leads, the at least one RF balun interposed on the cable trunk, and the cable trunk are made of non-ferrous material.

7. The ECG cable bundle of claim 1, wherein the at least one RF balun can be tuned for a proton Larmor frequency of a magnetic resonance (MR) scanner at a magnetic field of 1.5 T or 3 T MRI using a parallel resonant LCR circuit.

8. The ECG cable bundle of claim 1, wherein the ECG cable bundle is adapted to transfer ECG signals from a patient during performance of an MRI scan.

9. The ECG cable bundle of claim 1, wherein the ECG cable bundle is adapted to transfer ECG signals from a patient during performance of an MRI scan without interfering with magnetic resonance (MR) scanner operation.

10. The ECG cable bundle of claim 1, wherein the ECG cable bundle is adapted to electrically couple to the patient and receive ECG signals from the patient without interfering or inhibiting the performance of an MRI scan on the patient.

11. The ECG cable bundle of claim 1, wherein the plurality of electrodes are made of a porous activated carbon with silver-coated films in contact with a silver-chloride gel.

12. The ECG cable bundle of claim 1, wherein at least one of the plurality of connectors and the proximal connector includes a continuous shield to maintain zero emissions.

13. A method for performing an electrocardiography (ECG) on a patient during a magnetic resonance imaging (MRI) scan, comprising:
   placing a plurality of MRI-compatible electrodes on particular locations of the patient, the plurality of electrodes electrically coupled to distal ends of a plurality of signal leads, wherein the plurality of signal leads further comprise resistor pairs disposed at different locations, tuned for specific magnetic resonance imaging (MRI) energy, each of the plurality of electrodes being electrically coupled to a different one of each of the plurality of signal leads;
   performing the MRI scan of the patient connecting the plurality of MRI-compatible electrodes to an ECG cable bundle with a plurality of connectors disposed at the proximal ends of the plurality of signal leads, the plurality of connectors electrically and mechanically coupled to a yoke that is electrically and mechanically coupled to a first end of a cable trunk, with at least one radio frequency (RF) balun interposed on each of the plurality of signal leads between the plurality of electrodes and the yoke, and a proximal connector electrically and mechanically coupled to a second end of the cable trunk, with at least one RF balun interposed on the cable trunk between the yoke and a the proximal connector creating series of RF baluns; and
   simultaneous to performing the MRI scan, recording ECG traces.

14. The method of claim 13, wherein the particular locations comprise:
   a right arm (RA), a left arm (LA), a left leg (LL), a right leg (RL), a sternal edge right (V1), a sternal edge left (V2), mid-clavicular line left (V4), anterior axillary line (V5), between V2 and V4 (V3), and mid-axillary line left (V6) of the patient.

15. The method of claim 13, wherein the plurality of MRI-compatible electrodes are used for the ECG and do not interfere with the MRI scan.

16. The method of claim 13, wherein the use of the ECG and the plurality of MRI-compatible electrodes do not heat to a temperature that would burn the patient wearing the plurality of MRI-compatible electrodes during the MRI scan.

17. The method of claim 16, wherein the ECG and the plurality of MRI-compatible electrodes do not heat above 1.5 Celsius during a 4 Watt/kg Specific Absorption Rate (SAR) MRI scan.

* * * * *